US 6,590,200 B1

(12) United States Patent
Ludwig et al.

(10) Patent No.: US 6,590,200 B1
(45) Date of Patent: Jul. 8, 2003

(54) SYSTEMS FOR DETECTING MEASURING INCLUSIONS

(75) Inventors: Reinhold Ludwig, Paxton, MA (US); Diran Apelian, West Boylston, MA (US); Sergey Makarov, Worcester, MA (US)

(73) Assignee: Worcester Polytechnic Institute, Worcester, MA (US)

(*) Notice: Subject to any disclaimer, the term of this patent is extended or adjusted under 35 U.S.C. 154(b) by 0 days.

(21) Appl. No.: 09/285,528

(22) Filed: Apr. 2, 1999

(51) Int. Cl.[7] .............................................. H01J 40/14
(52) U.S. Cl. .................................................. 250/222.2
(58) Field of Search ........................ 264/227; 250/222.2

(56) References Cited

U.S. PATENT DOCUMENTS

| | | | |
|---|---|---|---|
| 3,466,154 A | | 9/1969 | Hori et al. ...................... 23/317 |
| 3,831,660 A | * | 8/1974 | William ........................ 164/418 |
| 4,786,320 A | * | 11/1988 | Hobson et al. ............. 75/10.65 |
| 4,909,836 A | * | 3/1990 | El-Kaddah ................... 266/227 |
| 5,102,449 A | * | 4/1992 | Ducrocq et al. ........... 75/10.18 |
| 5,198,749 A | * | 3/1993 | Guthrie et al. ............. 324/71.1 |
| 5,241,262 A | * | 8/1993 | Guthrie et al. ............. 324/71.1 |
| 5,604,301 A | | 2/1997 | Mountford et al. ........ 73/61.75 |
| 5,674,401 A | | 10/1997 | Dickert et al. .............. 210/695 |
| 5,788,819 A | | 8/1998 | Onishi et al. ............... 205/155 |
| 5,834,928 A | | 11/1998 | Doutre ........................ 324/71.4 |
| 5,985,674 A | * | 11/1999 | Umezawa et al. .......... 436/172 |
| 6,355,085 B1 | * | 3/2002 | Pillin et al. ................ 210/222 |

FOREIGN PATENT DOCUMENTS

| | | |
|---|---|---|
| GB | 737005 | 9/1955 |
| WO | 97/22859 | 6/1997 |
| WO | WO 97/28901 | 8/1997 |
| WO | 99/39183 | 8/1999 |

OTHER PUBLICATIONS

S. Makarov, et als., "Electromagnetic Visuasization Technique for Non–Metallic Inclusions in a Melt", Measur. Technol. 10, 1999, p. 1047–1053.

D. Apelian, "Advances in Metal Treatment of Aluminum and Foundry Alloys", Light Metals 1997.

K. Hoshino, et als., "The Filtration of Molten 1XXX Series Aluminum Alloys with Rigid Media Tube Filter", Light Metals 1996.

S. Makarov, et als., "Inclusion Removal in Molten Aluminum: Mechanical, Electromagnetic, and Acoustic Techniques", AFF Transactions, 1999, p. 727–735.

Sergey, Makarov, et als., "Electromagnetic Visuasization Technique for Non–Metallic Inclusions in a melt", Metal Processing Institute, WPI, Worcester, Massachusetts.

* cited by examiner

Primary Examiner—Zandra V. Smith
(74) Attorney, Agent, or Firm—Bowditch & Dewey, LLP

(57) ABSTRACT

The present invention relates to systems of methods of detecting and measuring inclusions in liquid metals. More particularly, non-metallic inclusions having a conductivity level different from the liquid metal melt are forced to migrate and are collected on a measurement surface using electromagnetic Lorentz forces. The inclusions and their concentrations are detected at the measurement surface using either an electrostatic detection system or an optical detection system.

35 Claims, 9 Drawing Sheets

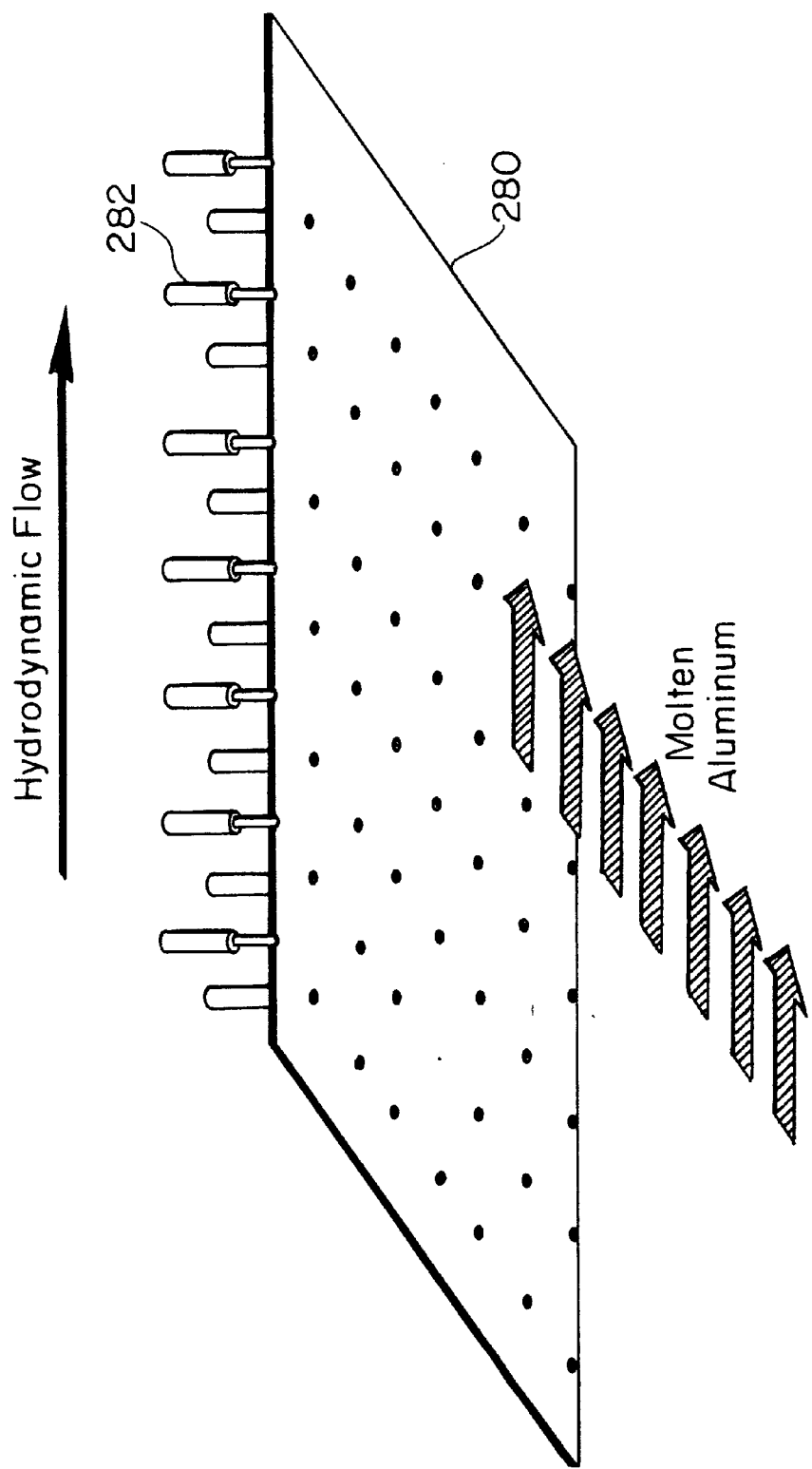

SYSTEMS FOR DETECTING MEASURING INCLUSIONS

BACKGROUND OF THE INVENTION

Due to the increasing demand for high quality metals, the purification of molten metals is becoming increasingly crucial. As a result, methods for the detection, measurement, separation and removal of inclusions from molten metals are desirable. In particular, the aluminum casting industry is in need of a reliable, fast, and economical detection system that enables furnace operators to conduct fine metal cleaning operations, and thus prevent small defects in the finished products.

A typical aluminum melt, for example, contains a large number of small non-metallic inclusions, less than or equal to 50 μm in size. These include particles of oxides ($Al_2O_3$), spinels ($MgAl_2O_4$), and carbides (SiC, $Al_4C_3$), with a higher melting point. Inclusions in alloys can impair the mechanical properties of articles made therefrom, are also detrimental to surface finish and machinability, increase internal porosity in the castings, as well as increase corrosion. Non-metallic inclusions act as stress-raisers, and can cause premature failure of a component.

The assessment of the level of inclusions present in the melt is one of the key parameters which needs to be measured in molten metal processing. The existing detection techniques include pressure filter test, acoustic emission detection, and electric resistivity Coulter counter. The first two methods mainly rely upon a qualitative distinction between heavily contaminated melts and a clean melt. The Coulter counter method evaluates both concentration and size distribution of inclusions larger than 15–20 μm for a small probe. However, this method is quite expensive and can only detect the effective size of an inclusion.

SUMMARY OF THE INVENTION

The present invention relates to a system for detecting and measuring non-metallic inclusions in molten metals. The methods for measuring inclusions in molten metals of the present invention include the steps of forcing the migration of the contaminant particles or inclusions onto a measurement region or surface using electromagnetic Lorentz forces, detecting the particles in the measurement region and determining particle size and concentration at the measurement surface.

Electromagnetic force mechanisms have been investigated and used for purposes of separation and removal of contaminants in liquid metals. However, the cleaning systems relying on electromagnetic forces are not very effective because a very low force density is typically generated in a large liquid metal melt volume which needs to be cleaned, resulting in a slow relative particle motion. In the present invention electromagnetic forces are used to detect and measure non-metallic inclusions in a liquid metal. A detector system uses a small inspection volume, thus allowing for the generation of large force densities. The present invention may also be used to separate inclusions from metals such as aluminum utilizing the basis of high electromagnetic force density in channels having small volumes.

In particular, a preferred embodiment utilizes permanent magnets and a direct current (DC) source to generate electromagnetic forces. In addition, the methods for the detection of inclusions utilize electrostatic detection of the particle concentration at the measurement region or surface through a multi-pin measurement configuration. Further, conditioning of the surface is required to overcome the surface tension forces that are responsible for preventing the inclusions from penetrating through the melt surface. By conditioning the surface, the particles penetrate the surface in order to be detected. The methods of conditioning the surface to enable particle detection can comprise a mechanical system or an acoustical vibration system or a combination of these two systems. A mechanical system can use, for example, a roller, to continuously stretch out the surface layer of the melt. An acoustical vibration system involves the shaking of the liquid melt surface at a particular resonance frequency, for example 10–40 Hz depending on the geometric size of the inspection volume, using an alternating current (AC) superimposed over the DC current flowing through the melt. The surface vibrations stimulate particle motion.

In another preferred embodiment of the present invention, the detection system is an optical system which features a solid state imaging device such as a charge-coupled-device (CCD). The CCD based detector system facilitates the electronic recording of the particles distributed over the surface aperture. Once the particles are collected on the measurement surface or free melt surface by the application of electromagnetic Lorentz forces, low-frequency acoustic vibrations are initiated to enable the migration of the particles through the metal melt. Recording of the particle size and distribution is performed with the CCD camera in conjunction with optical magnification of the region of interest using a lens system. The CCD camera may be coupled to an image acquisition system, which in turn may be coupled to a processor.

Yet another embodiment of the present invention uses only an AC power source to induce electromagnetic forces in the melt and thereby cause movement of the melt and consequent positioning of inclusions for measurement. The detection system can be used in conjunction with a system for the separation of inclusions from the melt and provide real-time feedback control of the processing operation.

The systems of the present invention provide for the quantitative measurement of small inclusions, and can determine particle shape. Further, the systems of the present invention can distinguish between a single particle and a cluster of particles, and can distinguish between gas bubbles and solid particles. There are several applications of the systems of the present invention including but not limited to the detection of inclusions in molten metals and the separation of inclusions from molten metals such as aluminum, ferrous materials, brasses and copper based alloys. In addition, the systems of the present invention may be utilized in semi-solid processing or die casting to homogenize segregated interdendritic liquid as well as breaking up dendritic networks.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 2F is a schematic diagram of another preferred embodiment of the detection system in accordance with the system of the present invention.

DETAILED DESCRIPTION OF THE INVENTION

The present invention is directed to systems and methods to detect and measure inclusions in liquid metals. Further embodiments involve the processing of liquid or semi-solid materials.

The systems and methods to detect and measure inclusions in liquid metals use electromagnetic forces to force the migration of the contaminant particles to a detection and measurement surface. The invention is predicated on the fact that the included particles have a different electric conductivity level than that of the liquid melt and as such are treated as being non-conducting as compared to the liquid melt. Thus, upon the application of a direct current (DC) throughout the melt with current density j and an imposed perpendicular magnetic flux density B, the Lorentz force density in the melt is $f=j \times B$, where the force density, current density and magnetic flux density are vector quantities and the force density is the vector cross product of the current density and the magnetic flux density. The Lorentz force is induced in the metal but not in the non-conducting inclusions since no current can propagate through them. As a reaction to this electromagnetic force (Newton's third law), the inclusions are equally forced in the opposite direction. The corresponding reaction force density $f_a$ on the non-conducting inclusions $f_a=-f$ is known as Archimedes electromagnetic force. Archimedes electromagnetic force is well suited for detection purposes since a detector uses a small inspection volume, where extremely large force densities can be obtained with corresponding rapid particle motion.

Figure 1A:
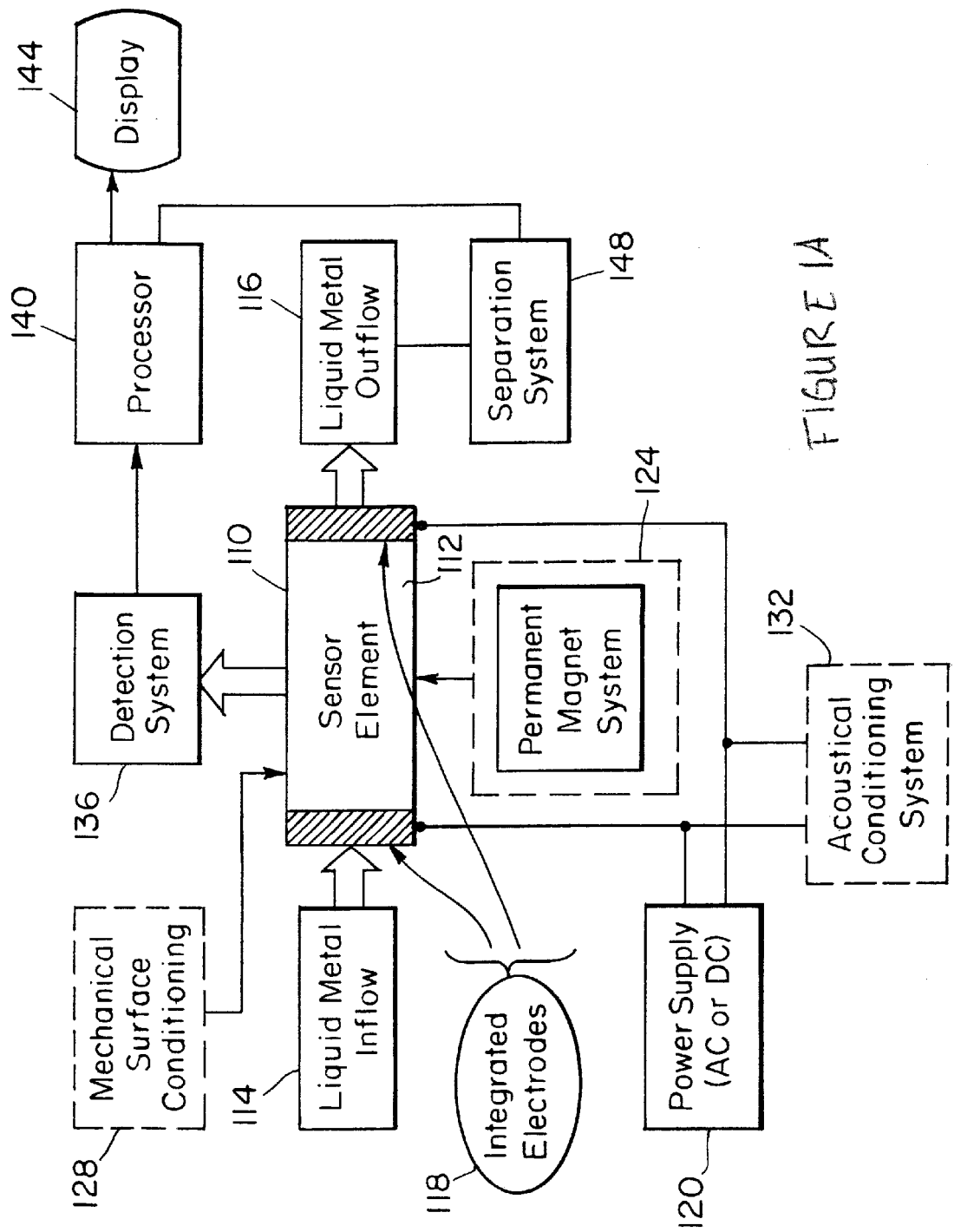
FIG. 1A is a schematic illustration of a system to provide liquid metal utilizing the system for detecting and measuring inclusions in accordance with the present invention.

Referring now to the drawings, FIG. 1A is a schematic illustration of a preferred method to provide liquid metal incorporating the system for detecting and measuring inclusions in accordance with the present invention. The particular sequence of steps describes the use of the system of the present invention in a system which provides liquid metal free of non-metallic inclusions. The metal is melted either in a reverbatory furnace or in an electrically heated furnace. Alternatively, the metal may be induction melted. The system comprises a sensor element 110 which consists of a container 112 into which flows a liquid metal having inclusions per step 114. The liquid metal flows out of the container per step 116 after the sensing and detection of the included particles has occurred. Electrodes 118 are integrated with the container 112 to provide a voltage drop in the container. An electromagnetic force is induced in the container which acts on the liquid metal and not on the included particles. The electromagnetic force can be generated by applying power supplied by the power supply 120, to the container. A DC current in combination with the permanent magnet system 124 can create the required electromagnetic force. Alternatively, the electromagnetic force can be generated by applying a high AC current also supplied by the power supply 120, whose self-induced magnetic field eliminates the need for the permanent magnet system 124.

The inclusions which are non-conducting as compared to the liquid metal rise toward a measurement region which is the free melt surface. Since the melt is not transparent in the visual domain the measurement region needs to be conditioned so as to force the inclusions to break through the melt surface which has a metal oxide layer disposed on it. To overcome the surface tension forces which retain the particles below the free melt surface, the measurement region may be conditioned mechanically per step 128, or by an acoustic conditioning system 132 or alternatively by a combination of the two.

The included particles are then detected by a detection system 136. The detection system may be an electrostatic measurement system or an optical detection system.

The results of the detection system are then recorded and particle size and concentration are computed in the processor 140. The results of the processing step 140 maybe displayed on a display 144 and used to monitor the size and concentration of inclusions. A particle separation system 148 is coupled to the computer to remove the detected inclusions to provide liquid metal free of inclusions.

Figure 1B:
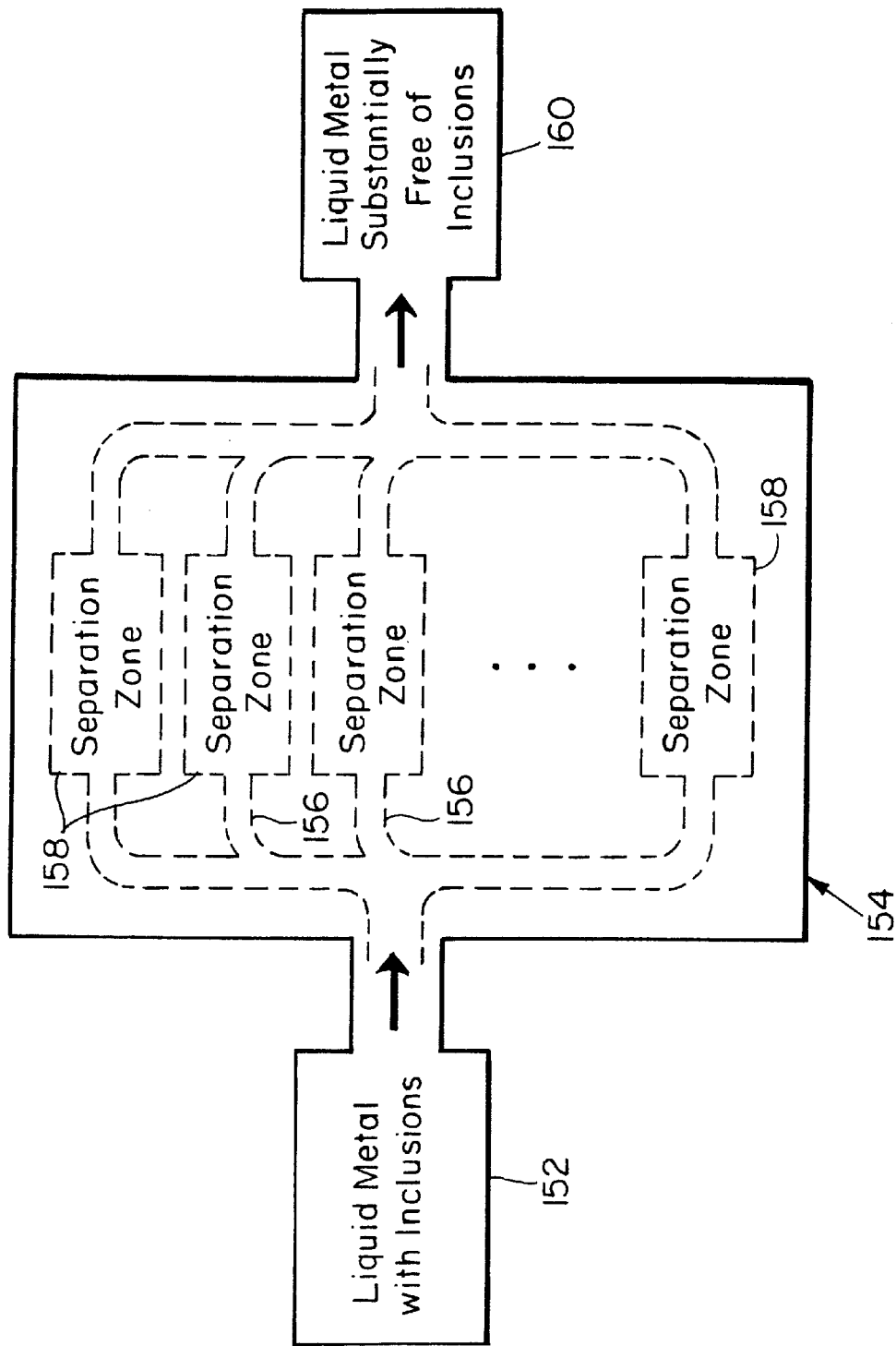
FIG. 1B is a schematic illustration of the system of the present invention being utilized as a separation system described in FIG. 1A.

FIG. 1B is a schematic illustration of the use of the present invention as a separation or cleaning system. A container 152 of liquid metal having inclusions feeds into a separation system 154. The separation system consists of small channels 156 for the liquid metal to flow into. The particles are separated in a separation zone 158 in each channel 156 by applying a high electromagnetic force density to the liquid metal in each channel. The resultant liquid metal that is collected from the separation system 154 in a container 160 is substantially free of inclusions. Each zone 158 or channel 156 can have a detector system as shown in FIG. 1A to provide monitoring of each channel.

Figure 1C:
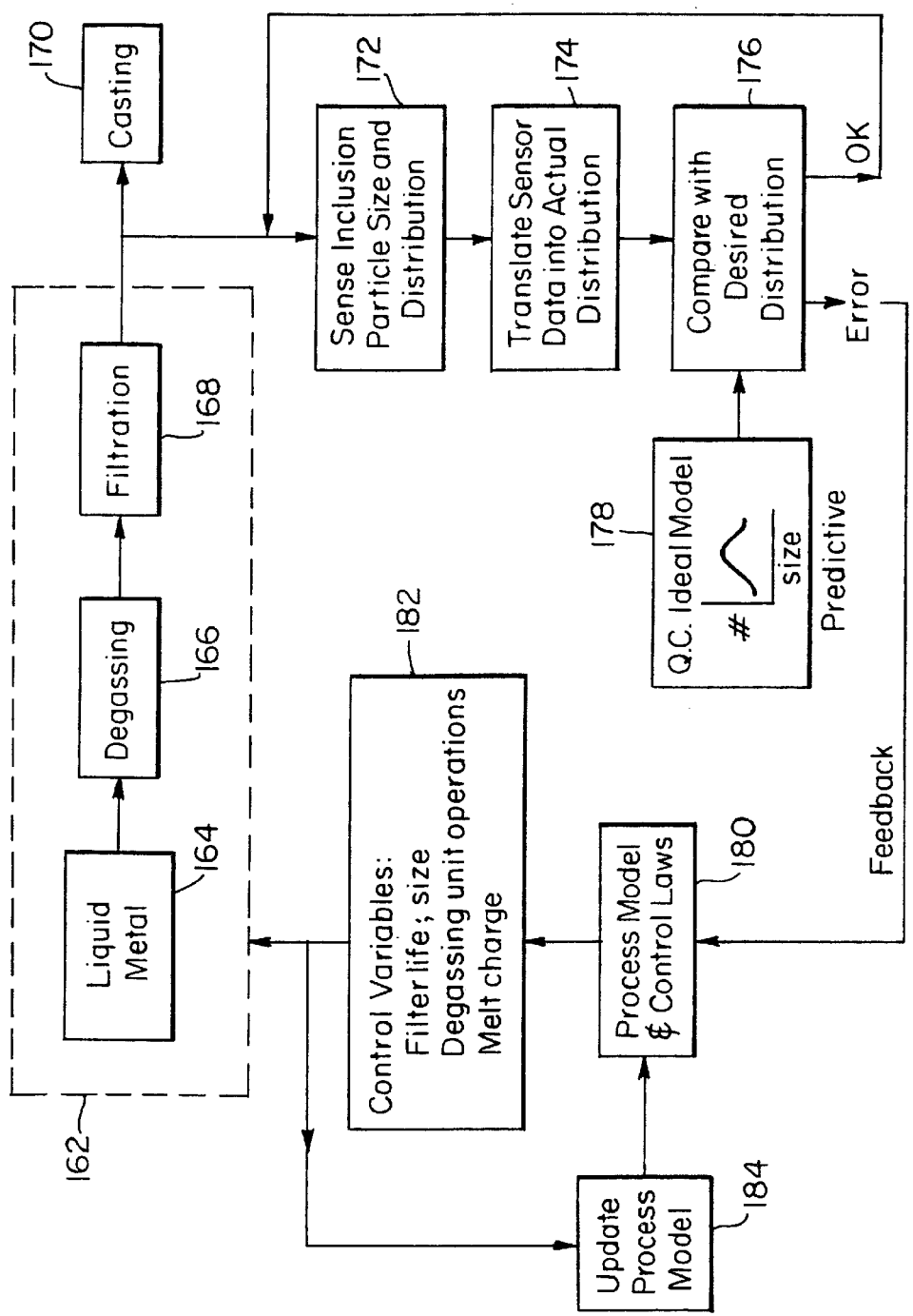
FIG. 1C is a flow chart describing the details of a molten metal processing system incorporating the system for detecting and measuring inclusions in accordance with the present invention.

FIG. 1C schematically illustrates further details of the utility of the present invention in a molten metal processing system 162 that supplies liquid metal, having reduced concentrations of larger inclusions or is substantially free of inclusions, for casting and other applications. The particular sequence of steps describes the system to provide inclusion free metal. Liquid metal in step 164 is degassed per step 166 to remove gaseous hydrogen, for example. The liquid metal then flows through a filtration system per step 168 to remove inclusions as part of a typical molten metal processing system. The resultant liquid metal is then used in a casting process per step 170. A certain small volume of the filtered liquid metal is fed into the detection and measurement system in accordance with the present invention per step 172. Step 172 senses inclusions and determines particle size and distribution. The sensor data is then translated into an actual distribution for the molten metal per step 174. The actual distribution of inclusions is then compared with a desired distribution per step 176. The desired, ideal distribution computed per a model such as predicted in step 178, is stored electronically in a memory and retrieved to perform the comparison per step 176. If the actual distribution of the inclusions is within an acceptable range of the desired distribution, no corrective action is taken. However, if the actual distribution of the inclusions is not within an acceptable range of the desired distribution then corrective action is initiated per the process model and control laws of step 180. The control variables listed in step 182, for example, filter life arid size, the operations of the degassing unit and the charge of the melt are then recalculated and changes are programmed into the processing system. As a result of changes made to the control variables, the process model is updated per step 184.

Figure 2B:
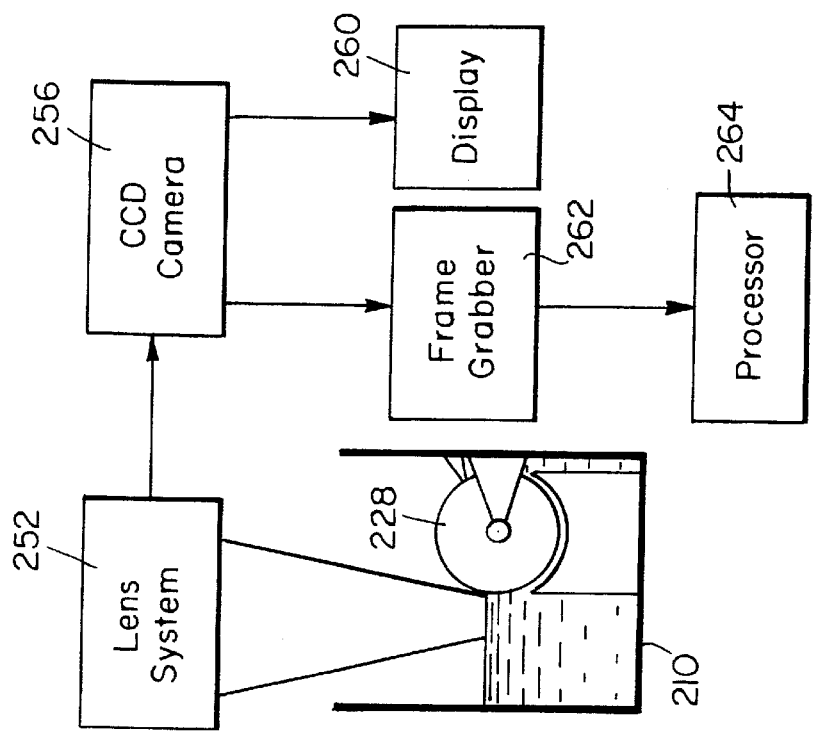
FIG. 2B is a schematic diagram of a preferred embodiment of the detection system to detect and measure inclusions in molten metals in accordance with the present invention.
Figure 2A:
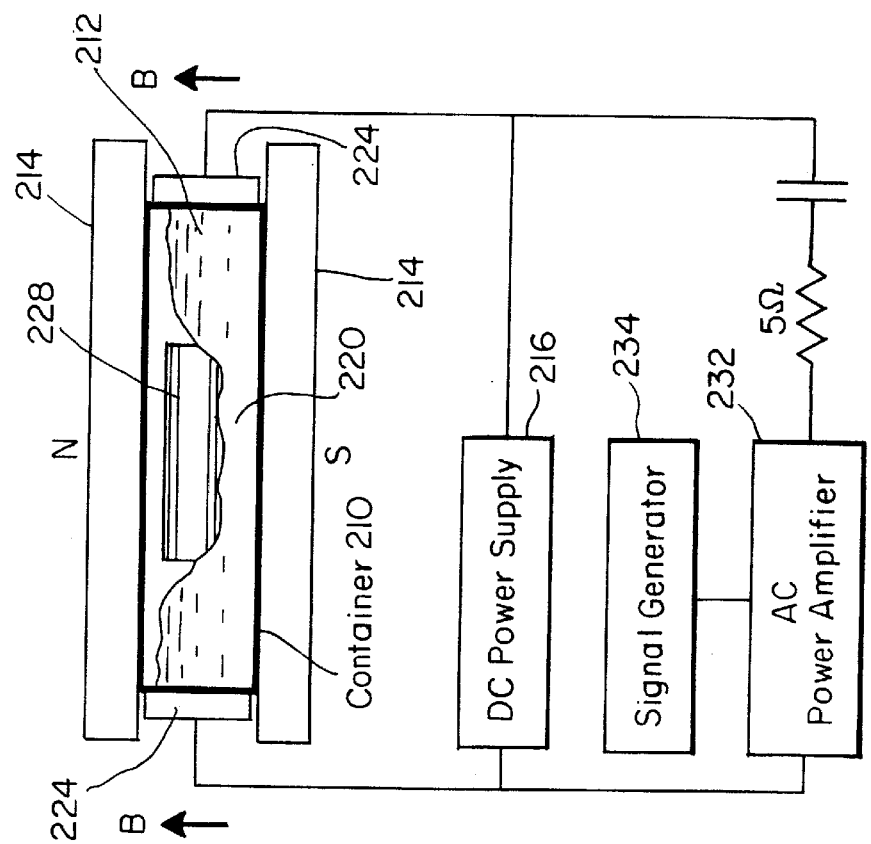
FIG. 2A is a schematic illustration of an embodiment of the system to measure inclusions in molten metals in accordance with the present invention.

FIG. 2A, is a schematic illustration of a preferred embodiment of the system to detect and measure inclusions which can be used to perform the methods of the present invention. A container 210, which for example is made of ceramic, is filled with the liquid melt 212, for example liquid gallium. The liquid melt 212 is subjected to both an electric as well as a magnetic field.

The resulting electromagnetic Lorentz force density is created by two permanent magnets 214 having a range of 0.3 Tesla to 0.6 Tesla and a DC current having a range of 100 A to 150 A supplied by a DC power supply 216. The magnetic field is nearly homogeneous in between the two electrodes 224. The system may be configured so that the melt continuously flows through the container 210 and the inclusions are collected on a region 220 of the free melt surface. If the flow cross-section is 0.5 by 1 cm, then the current density j is $2.4 \times 10^6$ A/m$^2$ based on a total current of 120 A. Accordingly, the Lorentz force density is $7.2 \times 10^5$ N/m$^3$ if the flux density is 0.3 Tesla. This is more than thirty (30) times the gravitation force density acting on the molten metal such as aluminum. Simultaneously, this is more than sixty (60) times the gravitation Archimedes force on spinel inclusions (p=3600 kg/m$^3$) in molten aluminum. These considerations underscore the fact that electromagnetic treatment is quite effective if the cross-sectional area for the metal flow is sufficiently small.

Coupled to both sides of the container 210 are electrodes 224. The electrodes may, for example, be made of copper. The electrodes provide the DC current flow which in combination with the magnetic field is responsible for the electromagnetic Lorentz force. In addition, the current flow encounters an electric resistance due to the presence of the liquid metal. As a consequence, a voltage drop is created between the electrodes which in turn can be measured through the placement of small copper point electrodes in contact with the free melt surface. Variations in the voltage drop between the adjustment point electrodes permit the detection of particles that migrated to the surface in response to the Lorentz force.

Non-conducting particles experience uniform longitudinal motion with constant velocity and, simultaneously, transverse motion, rising toward the free melt surface or region 220 with a given velocity. Even for inclusions of 10 μm in diameter, the rise velocity is sufficient to enable inclusion collection on a region of the free melt surface within a reasonable time duration. Since the melt is not transparent in the visual domain of the electromagnetic spectrum, inclusion escape on the free melt surface plays a decisive role. The main mechanism that prevents escape is surface tension. The Archimedes electromagnetic force is much smaller than the surface tension force, for all possible particle sizes. Thus, an additional treatment of the melt surface is necessary.

The surface is conditioned mechanically, by continuously stretching out the surface layer of the melt, for example by a rotating cylinder such as a ceramic roller 228. The roller drags the surface layer away from the detection region. This process makes the melt surface appear as if it is being "stretched" with new particles continuously appearing. Another method for conditioning the melt surface is acoustically vibrating the liquid melt surface in the range of 10–40 Hz depending on the geometric size of the inspection volume. This can be accomplished through an AC power amplifier supply 232 in the range between 500–800 W, and an AC signal generator 234 providing an AC current. An additional periodic Lorentz force component appears in the transverse direction, which produces surface vibrations. Such vibrations stimulate particle escape. Methods for providing oscillations of liquid metal by electromagnetic Lorentz forces are described in "Resonant oscillations of a liquid metal column driven by electromagnetic Lorentz force sources", by Sergey Makarov, Reinhold Ludwig and Diran Apelian, J. Acoust. Soc. Am., Vol 105, No. 4, April 1999, which is incorporated herein by reference. Methods described in the aforementioned reference publication can be used with the systems described herein to provide acoustic vibrations for conditioning the free melt surface.

Both methods for conditioning the surface have their advantages and disadvantages. Mechanical stretching implies moving sensor components, for example rollers, whereas acoustic vibration reduces the quality of the optical image formation. A combination of the two methods may be used to offset the disadvantages of the individual methods.

Based on an exemplary cylindrical volume, a current strength of 150 A (DC current) supplied through two electrodes to a measurement container of 20 mm in length and 5 mm in radius creates an average radial force density of 100 kN/m$^3$. This is sufficient to force 75% of the inclusions with an average 40 micron effective diameter to the surface, amounting to an inspection speed of 88 ml/min.

In a preferred embodiment illustrated in FIG. 2B, the detection system in accordance with the present invention is an optical detection system which may include optical magnification of the region of interest using a lens system 252, for example a microscope, a CCD camera 256 and a display 260. In addition, the CCD camera may be coupled to a frame grabber 262 which in turn is coupled to a processor 264. The optical detection method predicts non-conducting and low-conducting inclusions of an average diameter in the range of 5 to 50 microns in molten aluminum.

Figure 2D:
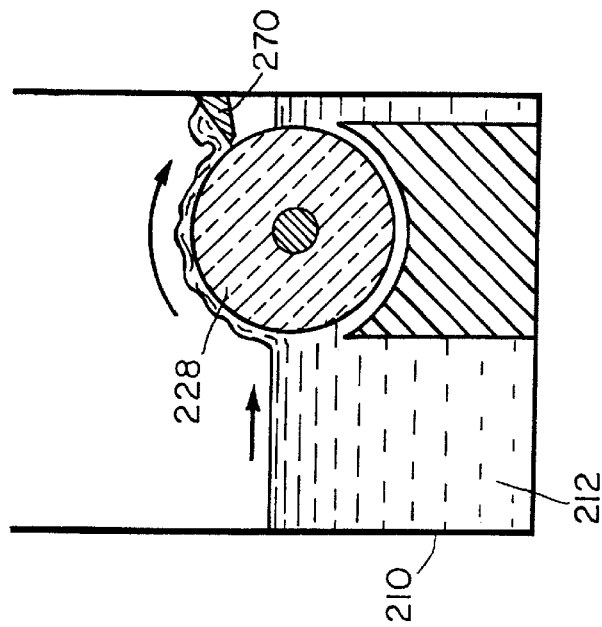
FIG. 2D illustrates a cross-sectional view of the container apparatus taken along lines 2D—2D of FIG. 2C.
Figure 2C:
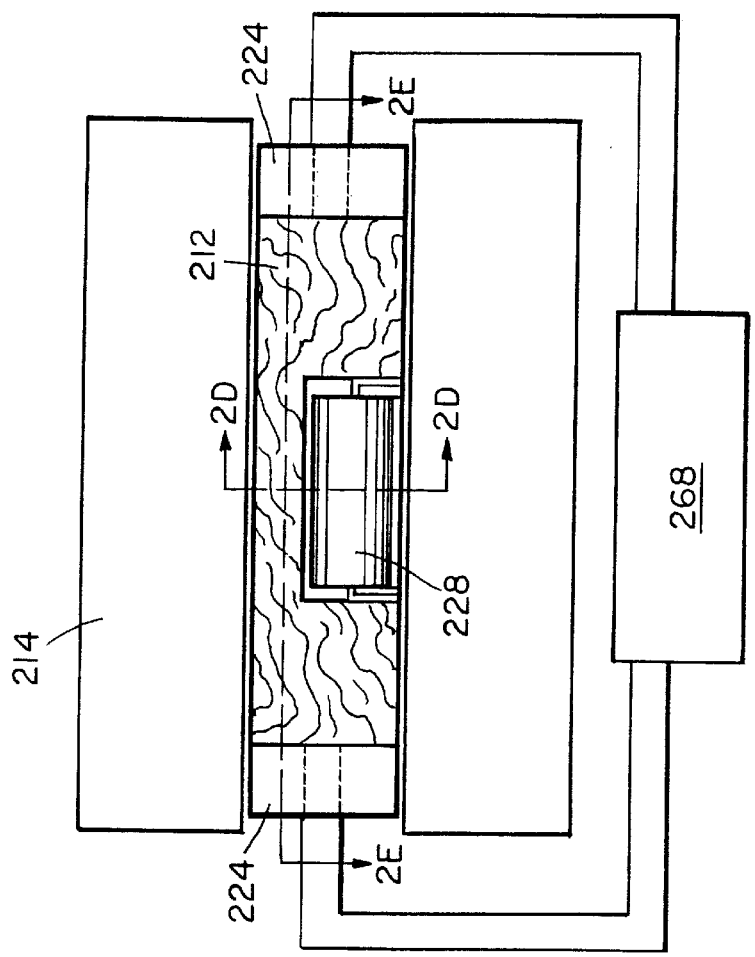
FIG. 2C illustrates the top view of the container apparatus shown in FIG. 2A.
Figure 2E:
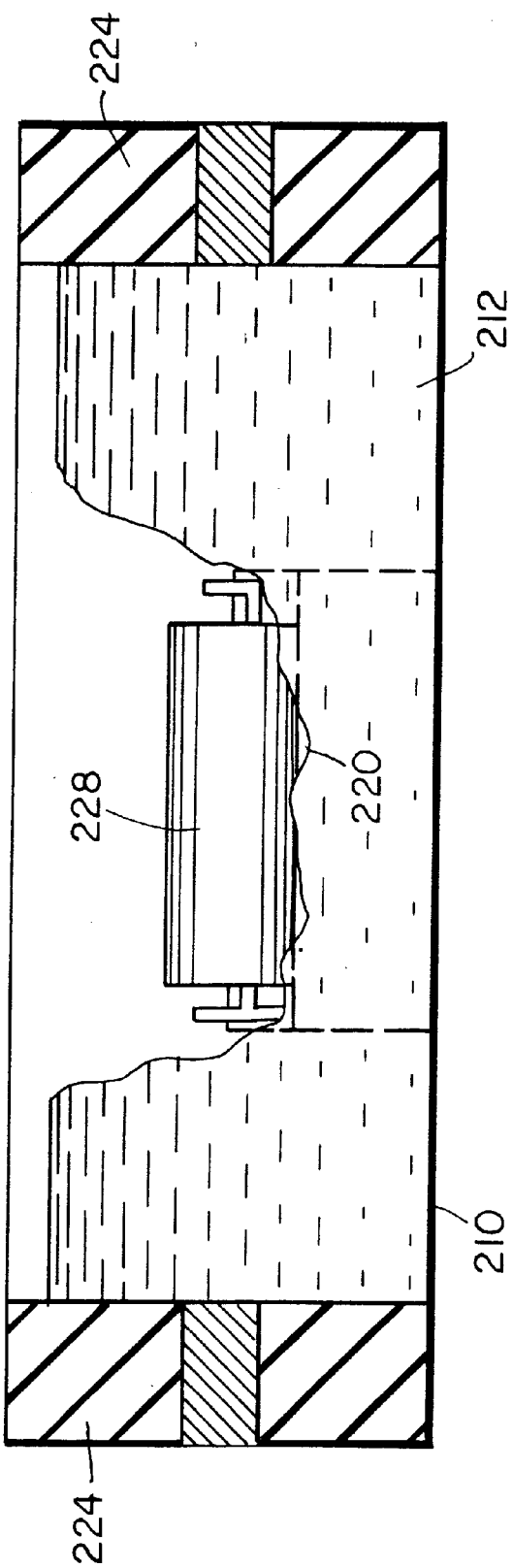
FIG. 2E illustrates a cross-sectional view of the container assembly taken along lines 2E—2E of FIG. 2C.

FIGS. 2C, 2D and 2E provide further details regarding the container assembly and the mechanical conditioning system described in FIGS. 1 and 2A. The roller stretches the free melt surface and in doing so disrupts the metal oxide layer that forms on the surface, which then enables the escape of the particles to the surface which allows for detection of the particles. The action of the mechanical roller tends to move a layer of the melt on top of the roller, potentially allowing for the separation of the included particles in the top layer into a baffle 270 shown in FIG. 2D.

FIG. 2F illustrates another embodiment of the detection system of the present invention. Once the particles reach the surface, this embodiment of the present invention uses an electrostatic measurement device 280 having voltage recording pins 282 in the range of 10 to 100 pins, deployed over the free melt surface to measure a differential voltage distribution which subsequently can be compared to a baseline distribution of pure molten aluminum. The pins may be small copper point electrodes in contact with the free melt surface. If the probe spacing is on the order of 0.3 mm using laser drilling, the approximate calculations indicate that the expected differential potential distribution should exceed 4 to 5 $\mu V$, well above the background noise. This detection system predicts nonconducting and low-conducting inclusions of an average diameter in the range of 20 to 100 microns in molten aluminum.

Figure 3A:
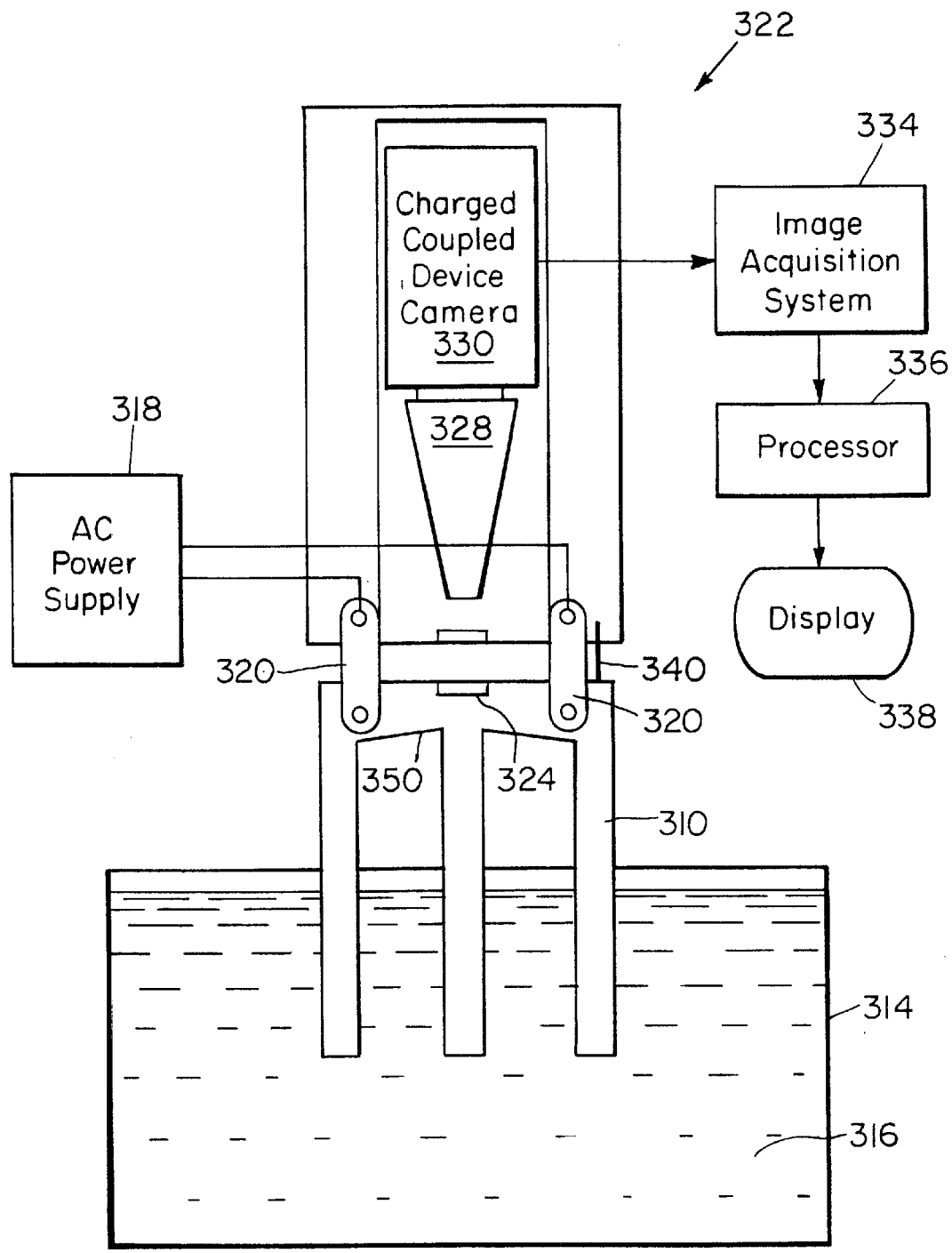
FIG. 3A is a schematic illustration of another preferred embodiment of the system in accordance with the present invention.

Referring to FIG. 3A, another preferred embodiment of the system to detect and measure inclusions in liquid metal includes a sensing element 310 consisting of three columns or sections which are placed in a container 314 filled with a liquid metal 316. The columns may be made from ceramic or a refractory material. An AC power supply 318 supplying a current in the range of 500 A to 1000 A is coupled to the electrodes 320 which are integrated with the sensing element 310.

The optical detection system 322 includes optical magnification of the region of interest 324 using a lens system 328, a CCD camera 330, an image acquisition system 334 coupled to a processor 336, and a display 338. A long focal length objective lens 328 with a magnification in the range of 1000 to 2000 is coupled to the CCD. The CCD based detector system facilitates the electronic recording of the particles distributed over the surface aperture. Low-frequency acoustic vibrations can be initiated through alternating Lorentz force using a modulating AC signal generator in conjunction with an AC power amplifier as previously described. Low-frequency acoustic vibration in the frequency range of 10–40 Hz break-up the surface layer (an oxide film plus surface tension forces) of the liquid melt, to allow the escape of the inclusions from the melt to facilitate detection.

The sensing element has a self-cleaning feature due to the angular relationship between the columns. A tilt angle 350 in the range of 2–5° allows the liquid melt to flow out of the sensing element 310 once the element is removed from the melt.

An inert gas supply 340 provides an inert carrier gas to remove any gaseous impurities to maintain a clean interface for the quartz window 324.

Figure 3B:
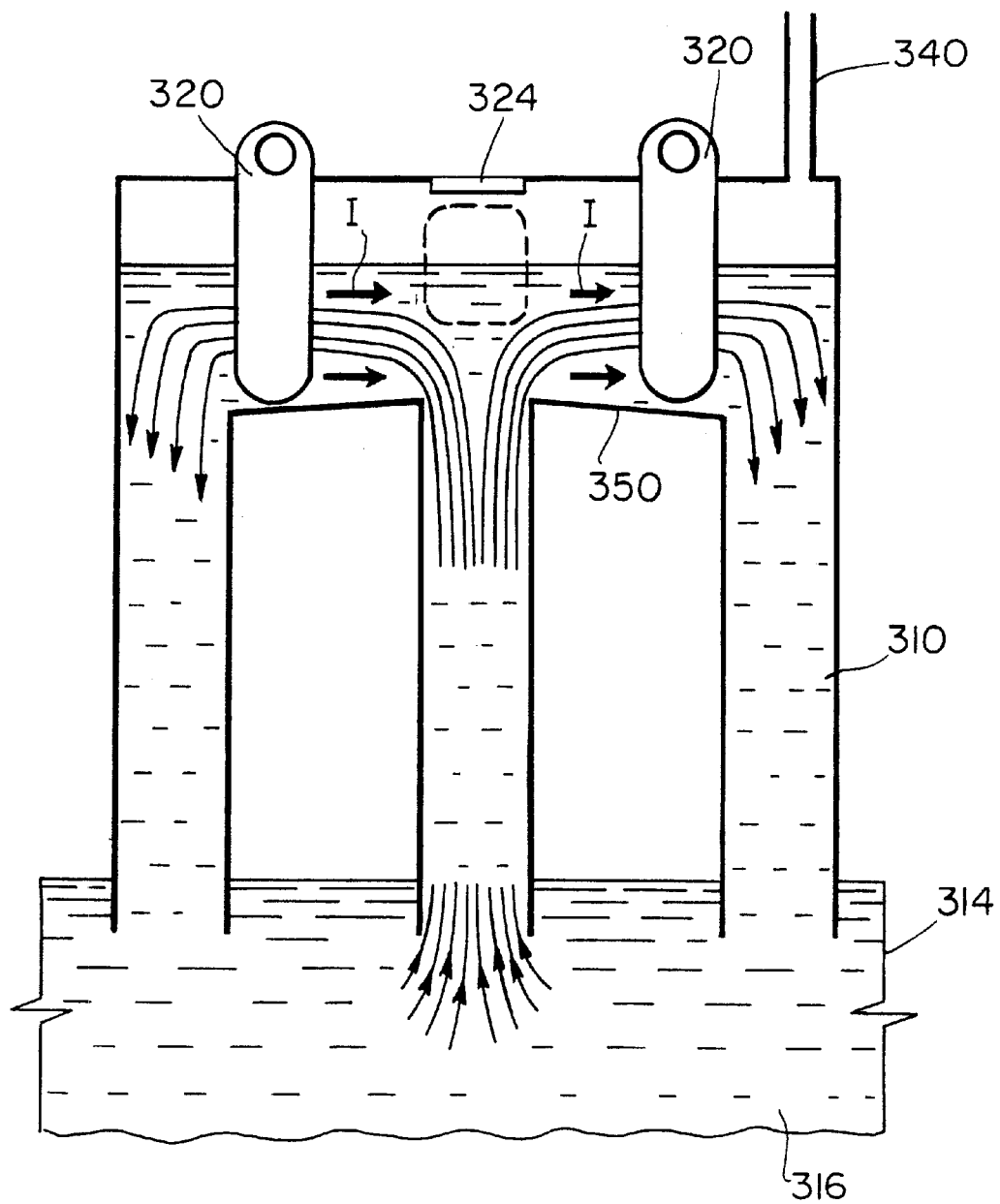
FIG. 3B is a detailed schematic illustration of the sensor element shown in FIG. 3A.

No permanent magnets are required for the embodiment as discussed with respect to FIG. 3A. Referring to FIG. 3B, which provides further details of the sensing element 310 illustrated in FIG. 3A, a sufficiently strong self-induced average magnetic-field in the range of 0.05 Tesla to 0.1 Tesla is initiated by the 60 Hz AC current of 1000–2000 Amperes when applied to the container. The total power applied is in the range of 2–3 kW. Although the self-induced magnetic field is weaker than the field provided by the embodiment having the permanent magnet system, the significantly higher current density as a result of the higher AC current is responsible for a strong electromagnetic Lorentz force density. It also may be possible to replace the power supply by a transformer. Additionally, another embodiment of the system of the present invention may use a removable sensor or sensing element made of tungsten as opposed to ceramic.

The advantage of the embodiment as illustrated by FIGS. 3A and 3B, is the creation of a self-induced magnetic field which eliminates the use of permanent magnets. Permanent magnets require an external cooling system which does not need to be provided for by the system described with respect to FIGS. 3A and 3B. In addition, a DC power supply which is typically move expensive and cumbersome to handle than an AC power supply, is not required to operate the system as disclosed with respect to FIGS. 3A and 3B. Further, the embodiment illustrated by FIGS. 3A and 3B eliminates the need for an external pump. Instead, the embodiment relies on a self-pumping mechanism to assure continuous melt flow through the measurement region.

The system of the present invention can be used to detect and measure inclusions in molten metal. Further application of the present invention is in the separation of inclusions from molten metals such as aluminum, ferrous, brasses and copper alloys. In addition, the systems of the present invention may be utilized in semi-solid processing or die casting to homogenize segregated interdendritic liquid as well as breaking up dendritic networks.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for detecting and measuring inclusions in a fluid metal, comprising the steps:

forcing the migration of contaminant particles in a fluid metal to a measurement region;

separately conditioning a surface of the fluid metal within the measurement region to facilitate penetration of the surface by the contaminant particles;

detecting the contaminant particles in the measurement region; and determining a concentration of the contaminant particles in the fluid.

2. The method according to claim 1, wherein the step of forcing the migration of the contaminant particles comprises applying electromagnetic Lorentz force density.

3. The method according to claim 2, wherein the electromagnetic Lorentz force density is applied using a plurality of permanent magnets and a direct current (DC) source.

4. The method according to claim 2, wherein the high electromagnetic Lorentz force density is applied using an alternating current (AC) source.

5. The method according to claim 1, wherein the step of detecting the particles uses an electrostatic measurement.

6. The method according to claim 1, wherein the step of detecting the particles uses an optical detection system that detects the inclusions.

7. The method of claim 1, wherein the step of separately conditioning the surface within the measurement region comprises vibrating the measurement region.

8. The method of claim 1, wherein the step of separately conditioning the surface within the measurement region comprises applying a mechanical force to the surface.

9. A method for detecting and measuring inclusions in a fluid metal, comprising the steps:

forcing the migration of contaminant particles in a fluid metal to a measurement region;

conditioning the measurement region by applying a mechanical force to a surface of the fluid metal in the measurement region to facilitate penetration of the surface by the contaminant particles;

detecting the contaminant particles in the measurement region; and determining a concentration of the contaminant particles in the fluid.

10. The method according to claim 9, wherein the conditioning of the measurement region further comprises applying a mechanical force to the surface of the measurement region using a roller.

11. The method according to claim 9, wherein the conditioning of the measurement region is accomplished by vibrating the region.

12. The method according to claim 9, wherein the step of forcing the migration of the contaminant particles comprises applying electromagnetic Lorentz force density.

13. The method according to claim 12, wherein the electromagnetic Lorentz force density is applied using a plurality of permanent magnets and a direct current (DC) source.

14. The method according to claim 12, wherein the high electromagnetic Lorentz force density is applied using an alternating current (AC) source.

15. The method according to claim 9, wherein the step of detecting the particles uses an electrostatic measurement.

16. The method according to claim 9, wherein the step of detecting the particles uses an optical detection system that detects the inclusions.

17. Apparatus for measuring inclusions in a liquid metal, comprising:
   a container filled with a liquid metal;
   a plurality of electrodes, positioned relative to the container that provides a current path in the liquid metal;
   an acoustical vibrator positioned relative to the container to vibrate a surface of the liquid metal;
   a current generator connected to said electrodes; and
   a detection device that detects a size and concentration of inclusions in the liquid metal, the detection device positioned to examine a portion of the surface of the liquid metal to detect inclusions that flow through the portion of the surface.

18. The apparatus according to claim 17, wherein the current generator is a direct current (DC) source.

19. The apparatus according to claim 17, wherein the current generator is an alternating current (AC) source.

20. The apparatus according to claim 18, further comprising a plurality of permanent magnets to a create magnetic field.

21. The apparatus according to claim 17, wherein the detection device is an electrostatic device system.

22. The apparatus according to claim 17, wherein the detection device is an optical detection system.

23. The apparatus according to claim 22, wherein the optical detection system further comprises, an optical magnifier to magnify the measurement surface and a solid-state imaging device.

24. The apparatus according to claim 23, wherein the optical detection system is coupled to a display.

25. Apparatus for measuring inclusions in a liquid metal, comprising:
   a container filled with a liquid metal;
   a plurality of electrodes, positioned relative to the container that provides a current path in the liquid metal;
   a mechanical device positioned relative to the container that provides a mechanical force to a surface of the liquid metal;
   a current generator connected to said electrodes;
   a detection device that detects a size and concentration of inclusions in the liquid metal, the detection device having a plurality of electrodes positioned on a portion of the surface of the liquid metal to detect changes in voltage as the inclusions flow through the portion of the surface between said electrodes.

26. The apparatus according to claim 25, wherein the current generator is a direct current (DC) source.

27. The apparatus according to claim 25, wherein the current generator is an alternating current (AC) source.

28. The apparatus according to claim 26, further comprising a plurality of permanent magnets to create a magnetic field.

29. The apparatus of claim 25, wherein the mechanical device is a roller.

30. Apparatus for measuring inclusions in a liquid metal comprising:
   a container filled with a liquid metal having inclusions;
   an electrode system positioned relative to the container to provide a current path in the liquid metal;
   a conditioning device positioned relative to the container to at least one of apply a mechanical force and acoustical vibrations to a surface of the liquid metal;
   a current source connected to said electrodes; and
   an imaging device to sense inclusions in the liquid metal, the imaging device positioned to view a portion of the surface of the liquid metal to detect changes in the portion of the surface as the inclusions flow through the portion of the surface.

31. The apparatus of claim 1 further comprising an optical system that optically couples a surface of the liquid to the imaging device.

32. A method for measuring inclusions in a liquid metal, comprising:
   providing a container filled with a liquid metal and a plurality of electrodes;
   positioning the electrodes relative to the container to provide a current path in the liquid metal;
   attaching a current generator to the electrodes;
   separately conditioning a surface of a portion of the liquid metal to facilitate penetration of the surface by inclusions in the liquid metal;
   providing a detection device to measure a size and concentration of inclusions in the portion of the liquid metal; and
   measuring inclusions in the liquid metal.

33. The method of claim 30, further comprising:
   providing the detection device with a plurality of electrodes positioned on a measurement surface; and
   detecting changes in voltage as the inclusions flow through the measurement surface between the electrodes.

34. The method of claim 32, wherein the step of separately conditioning the surface comprises vibrating the portion of the liquid metal.

35. The method of claim 32, wherein the step of separately conditioning the surface comprises applying a mechanical force to the surface.

* * * * *

UNITED STATES PATENT AND TRADEMARK OFFICE
CERTIFICATE OF CORRECTION

PATENT NO. : 6,590,200 B1
DATED : July 8, 2003
INVENTOR(S) : Reinhold Ludwig, Diran Apelian and Sergey Makarov It is certified that error appears in the above-identified patent and that said Letters Patent is hereby corrected as shown below:

Column 10,
Line 29, please replace "claim 1" with -- claim 30 --
Line 48, please replace "claim 30" with -- claim 32 --

Signed and Sealed this

Sixteenth Day of March, 2004

JON W. DUDAS
*Acting Director of the United States Patent and Trademark Office*